United States Patent [19]

Hofling

[11] Patent Number: 5,419,777
[45] Date of Patent: May 30, 1995

[54] CATHETER FOR INJECTING A FLUID OR MEDICINE

[75] Inventor: Berthold Hofling, Wessling, Germany

[73] Assignee: Bavaria Medizin Technologie GmbH, Wessling/Oberpfaffenhofen, Germany

[21] Appl. No.: 235,900

[22] Filed: May 2, 1994

[30] Foreign Application Priority Data

Mar. 10, 1994 [DE] Germany .................. 44 08 108.1

[51] Int. Cl.⁶ .............................................. A61M 5/00
[52] U.S. Cl. .................................... 604/264; 604/164; 128/831
[58] Field of Search ............... 604/264, 164, 198, 187, 604/51-55, 165-169; 128/831

[56] References Cited

U.S. PATENT DOCUMENTS

| | | |
|---|---|---|
| 3,598,119 | 8/1971 | White . |
| 4,136,695 | 1/1979 | Dafoe .................. 128/831 |
| 4,578,061 | 7/1984 | Lemelson . |

FOREIGN PATENT DOCUMENTS

| | | |
|---|---|---|
| 8913761 U | 5/1990 | Germany . |
| 9210142 | 6/1992 | WIPO . |
| 9408653 | 4/1994 | WIPO . |

Primary Examiner—John D. Yasko
Attorney, Agent, or Firm—Klaus J. Bach

[57] ABSTRACT

An injection catheter including a catheter stem, a catheter tip, and a bundle of injection needles, wherein either the catheter tip is axially displaceable relative to the catheter shaft or the catheter tip is fixedly connected to the catheter stem and the bundle of injection needles is longitudinally displaceable relative to the catheter tip. The catheter tip may take various forms, as the injection needles within the catheter stem may take various forms and may be guided in various ways. An operating device is provided for effecting relative movements between the injection needles and the catheter tip, which operating device comprises two parts that are controllably displaceable relative to one another, thereby to cause the injection needles to be exposed or retracted. The operating device also includes inlets allowing medication to be applied through the injection needles.

12 Claims, 4 Drawing Sheets

CATHETER FOR INJECTING A FLUID OR MEDICINE

BACKGROUND OF THE INVENTION

The invention relates to a catheter for injecting a fluid or medicine into hollow organs and body cavities, particularly into coronary vessels and arteries, comprising: a catheter tip adapted to be inserted into arteries; a catheter stem; a plurality of injection needles arranged in the catheter tip so as to permit relative movement therebetween, said injection needles having their needle points disposed inside the catheter tip in a retracted position and having them protruding from the catheter tip in an exposed position for applying said fluid or medicine; an operating device mounted on the extracorporal end of the catheter for effecting said relative movement; and openings formed in the catheter tip allowing the injection needles to protrude laterally as well as forwardly; said catheter stem being affixed to one pan of the operating device and the injection needles being affixed to the other part thereof such that relative movement of the two parts toward one another will cause the catheter tip and the injection needles to be displaced one relative to the other so as to move the injection needles from said retracted position to said exposed position.

U.S. Pat. No. 3,598,119 discloses a medical instrument for administering an anaesthetic, wherein an injection needle is guided in an inner coaxial lumen for insertion of the needle under the skin, and a bladder at the distal region can be inflated through an outer coaxial lumen for holding the needle point fixed in position beneath the skin.

The German utility model No. G 89 13 761 discloses an endoscopic injection device for a fibrin agglutinant (FIBRINKLEBER) utilizing three coaxial tubes, the outer one of which serves as a guide for the two inner tubes employed to introduce a two-component fibrin agglutinant which, after commingling at the distal region of the tubes, is applied through an injection needle attached to one of the coaxial tubes.

WO 92 10 142 discloses a catheter including a multi-lumen catheter stem in which needles are longitudinally movable to extend them through openings in the catheter tip and thereby insert them into surrounding tissue for the purpose of introducing therein, through the needles, fiber-optical elements or thermic measuring elements, as the case may be. The hollow needles are suitable for use in inserting flushing and suction appliances.

U.S. Pat. No. 4,578,061 discloses a catheter for injecting a liquid into a vein or artery through an extendible injection needle which is longitudinally movable in the front end of the catheter and communicates with the axial lumen of the catheter so as, when extended, to receive therefrom medication supplied thereto. A two-chamber system provided within the catheter tip and including two coaxial plungers which are telescopically movable one within the other allows one of the plungers to be employed to extend the injection needle, and allows the other plunger to be utilized for applying a predetermined dose of medication through the injection needle.

PCT/EP93/02,829 discloses a catheter of the kind mentioned herein initially. This catheter utilizes a plurality of injection needles which are longitudinally movable in a multi-lumen stem connected to the catheter tip through a sleeve mounted and cemented thereon.

Since a catheter to be used in treating coronary vessels and arteries must be relatively long and, generally, may be about 1.2 m to 1.6 m in length, there will be a considerable amount of friction generated if a plurality of injection needles within the individual lumens of the multi-lumen stem must be moved over the full length of the catheter. If a multi-lumen tube made of a plastics material is being used, such relatively high friction generated over such great length can also create a problem insofar as it may result in undesirable longitudinal elongation or compression making it difficult for the injection needles to be precisely positioned within tissue.

It is the principal object of the invention to obviate these drawbacks.

SUMMARY OF INVENTION

An injection catheter including a catheter stem, a cathetertip, and a bundle of injection needles, wherein either the catheter tip is axially displaceable relative to the catheter shaft or the catheter tip is fixedly connected to the catheter stem and the bundle of injection needles is longitudinally displaceable relative to the catheter tip. The catheter tip may take various forms, as the injection needles within the catheter stem may take various forms and may be guided in various ways. An operating device is provided for effecting relative movements between the injection needles and the catheter tip, which operating device comprises two pans that are controllably displaceable relative to one another, thereby to cause the injection needles to be exposed or retracted. The operating device also includes inlets allowing medication to be applied through the injection needles This arrangement allows surface friction to be greatly reduced to an extent according to the design of the catheter head or the bundle of injection needles, respectively, thereby enabling a precise positioning of the injection needles within tissue.

In one particular embodiment of the invention, the bundle of injection needles is inserted, behind the distal region of the catheter, in a flexible tube of larger inside diameter and is movable in the catheter stem together with said tube. This arrangement has the advantage that there are only two tubular lumina that coaxially move relative to each other and which, due to the way in which they are designed and regardless of whether they are made of suitable plastics materials or metals, will undergo no undesirable longitudinal elongation or compression and thus, owing to the small amount of friction generated between the two coaxially movable lumina, will allow the injection needles to be properly positioned with little effort. Provision is made for the bundle of injection needles to extend, between the catheter head and the coaxial lumina, in bundled form over a length assuring, in conjunction with the good flexibility of the bundled injection needles, a high degree of flexibility of the distal section of the catheter.

In order to increase the distal flexibility of the catheter further still, the individual injection needles preferably have thinner walls, yet the same diametric flow volumes, in the distal region thereof so as to make them thinner and, hence, more flexible. The portions of the injection needles having the thicker walls may either extend throughout their whole length through a tubular outer stem or may be cemented or soldered in place inside a tubular inner lumen providing a larger diametric flow volume all the way to the operating device. This will result in considerable over-feed of fluid to the injection needles and, therefore, will allow the fluid to be applied evenly.

In accordance with a further embodiment of the invention, the catheter stem may have a stainless-steel mesh molded therein, or a stabilizing wire may be incorporated in the catheter stem or the multi-lumen bundle, respectively, in order to provide improved stability against undesirable longitudinal elongation or compression.

In order to facilitate the proper positioning or directed guiding of the catheter, there may be provided a guide wire guided in a guide lumen enveloped by the bundle of injection needles. This guide lumen may also be located eccentrically between the bundle of needles and the outer stem of the catheter, with the guide wire exiting extracorporally ahead of the operating device. If the catheter has no guide lumen, a guide wire may be secured to the distal end of the catheter tip.

In accordance with still another embodiment resulting in very little friction throughout the length of the catheter, the bundle of injection needles is affixed to the catheter stem interiorly thereof or the injection needles are affixed to a multi-lumen stem within the individual lumens thereof, an operating wire for retracting and extending the catheter tip respectively into and from the catheter stem extending through a guide lumen provided within the catheter stem. In order to minimize the friction produced in guiding the injection needles within the catheter tip, the catheter tip may consist of a bundle of stainless-steel tubes defining lumina through which extend the injection needles and, if desired, a guide wire. This type of catheter tip is particularly suitable for use with pre-bent injection needles or with needles made of a material which is superelastic and/or has shape-memory properties. A particularly advantageous manner of guiding the injection needles within the catheter tip is also obtained by inserting the bundle of injection needles through a central bore formed in the catheter tip and by having the injection needles laterally issue through guide slots communicating with the central bore.

Obviously, if the catheter tip has therein a plurality of guide lumina, not all of these need necessarily be occupied by injection needles. Rather, some of them may be available to receive photoconductors for conducting luminous energy through the catheter and to tissue, as needed to activate photo-energizeable substances, if used. Or they may be utilized to insert control and/or measuring systems. In case photoconductors are to be employed, the operating device will have to be suitably modified so as to provide direct access therethrough to the lumina intended to receive the photoconductors. However, provision also is made for the guide lumina to terminate extracorporally before the operating device so as to enable the photoconductors, or also a guide wire, to be inserted into the catheter.

The operating device for such a catheter includes a thrust plunger for the injection needles or the operating wire, which thrust plunger has a threaded portion thereof threadedly engaged with a knurled nut rotatable to effect axial movement of the plunger, the operating devices also including medication ports communicating with the individual injection needles. It is also possible, however, to control the thrust movements of the thrust plunger pneumatically, hydraulically or electrically by providing the operating device with suitable drive means. Provision may also be made for operating the thrust plunger by foot. Such non-manual kinds of thrust-plunger drives are of particular advantage if the operating device is provided with several medication ports. Preferably, the operating device is provided with a scale permitting the movements of the thrust plunger to be closely controlled. Stops may be provided for limiting the movement of the thrust plunger.

For special applications, the injection catheter may have attached thereto, distally and/or also proximally with respect to the catheter tip, a balloon for holding the catheter in a fixed position during an injection, and also an angioplastic balloon permitting a dilatation to be performed simultaneously with the injection.

The injection needle lumina may serve for inserting control and measuring appliances. Such appliances may include, for example, angioscopes, ultrasonic measuring devices, spectroscopes, devices for measuring activities, concentrations and PH-values, thermometers, and the like. Of course, the injection catheter can also be applied through puncture canals for the purpose of treating, for example, tumors, metastases, inflammation sites, convolutions or the like. Further advantages and features of the invention will become apparent from the following description of preferred embodiments read in conjunction with the claims and drawings.

BRIEF DESCRIPTION OF THE DRAWINGS

FIG. 4 shows a catheter tip composed of a bundle of tubes and fixedly connected to a single-lumen stem having a bundle of injection needles movably extending there through;

FIG. 7 shows a further embodiment of a catheter tip; and

DESCRIPTION OF THE PREFERRED EMBODIMENTS

Figure 1:
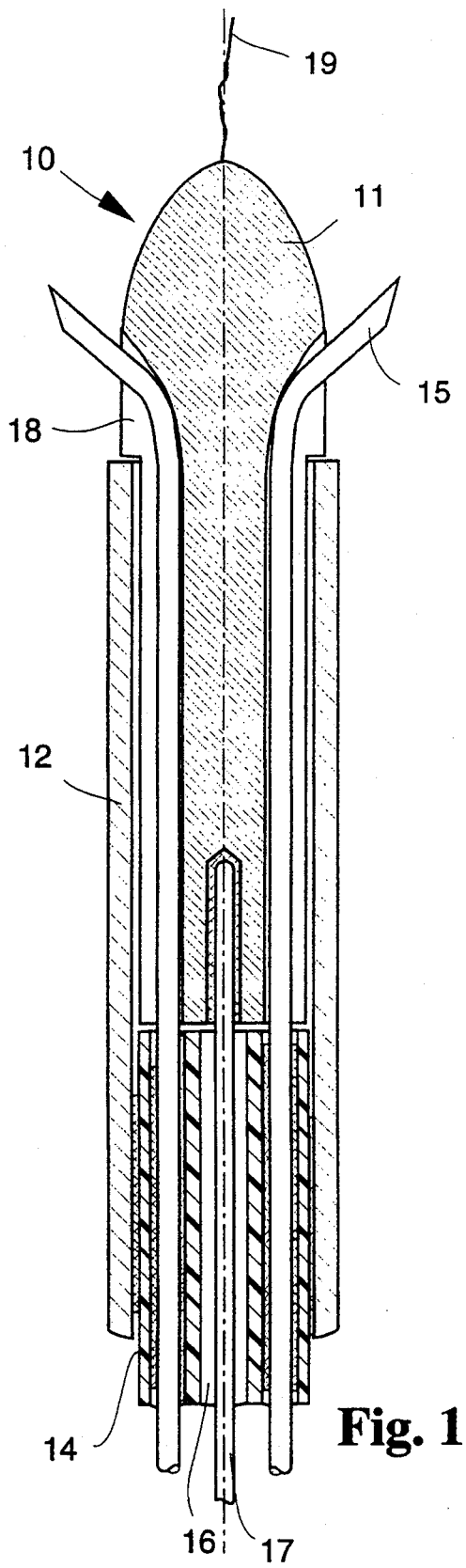
FIG. 1 shows a catheter tip which is movable in a catheter shaft to effect retraction and extension of injection needles mounted in bundled form within several lumina defined in the catheter stem.

FIG. 1 illustrates the distal end structure 10 of a catheter including a catheter tip 11 which is axially movable in a supporting sleeve 12 which is connected to a multi-lumen stem 14 having injection needles 15 secured thereto within the various lumina. Guided within a central guide lumen 16 is an operating wire 17 which is anchored to the catheter tip 11 and by means of which the latter can be axially displaced. In FIG. 1, the catheter tip is shown in a retracted position in which the injection needles 15 extending through longitudinal guide grooves 18 of the catheter tip are deflected outwardly to exposed positions thereof in which they can puncture tissue surrounding the catheter. Preferably, the injection needles are pre-bent at their distal ends so as to facilitate their being deflected outwardly by cam surfaces formed in the various guide grooves. The needles are preferably made of stainless steels or special alloys lending them enough flexibility to be deflectable outwardly through the action of the catheter tip, yet making them also stiff enough to penetrate tissue. Tissue penetration can be optimized through use of suitably ground needles.

Figure 2:
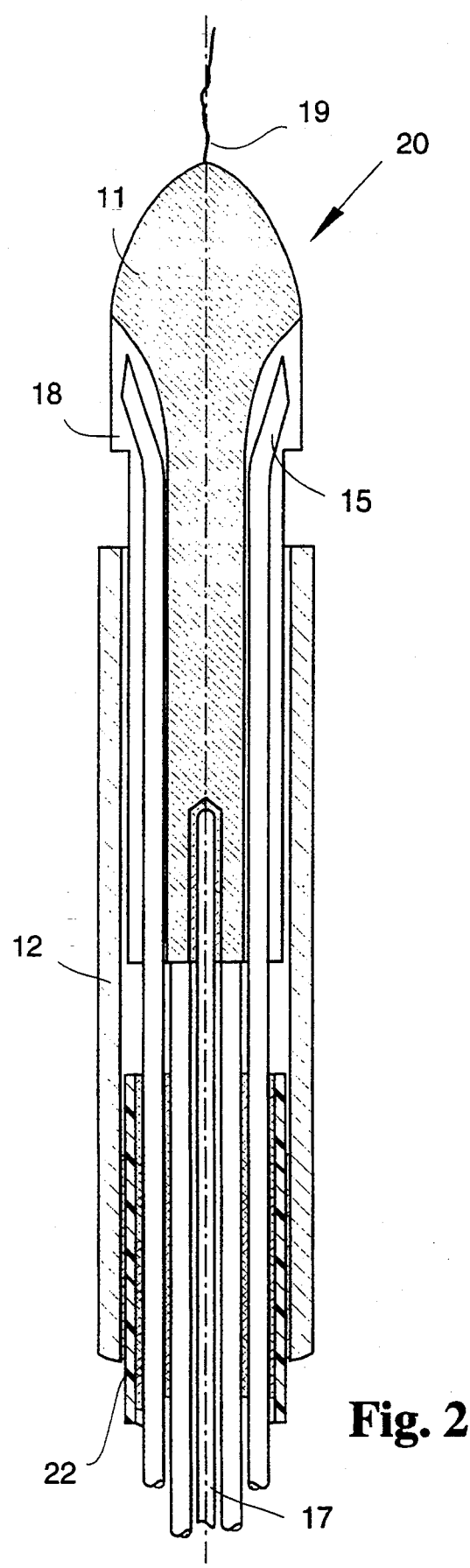
FIG. 2 shows a catheter tip together with retracted injection needles mounted in bundled form within a single-lumen stem.

In FIG. 2 illustrating a modification of the distal end structure 20 of the catheter, the catheter tip 11 is shown displaced forwardly to an extended position in which the injection needles 15 are disposed completely inside the guide grooves 18. This is the position for inserting the catheter into an artery or vein, such insertion being facilitated by a guide or so-called fixed wire 19 attached to the front or leading end of the catheter. In the catheter shown in FIG. 2, the injection needles 15 are likewise combined in a bundle and, as such, are secured to a single-lumen stem 22 interiorly thereof. The operating wire 17 extends movably through the inner space defined by the bundle of injection needles, and is guided by the needles. It is anchored to the catheter tip 11 and is axially movable to extend the catheter tip from or to retract it into the distal end portion of the catheter.

Figure 3:
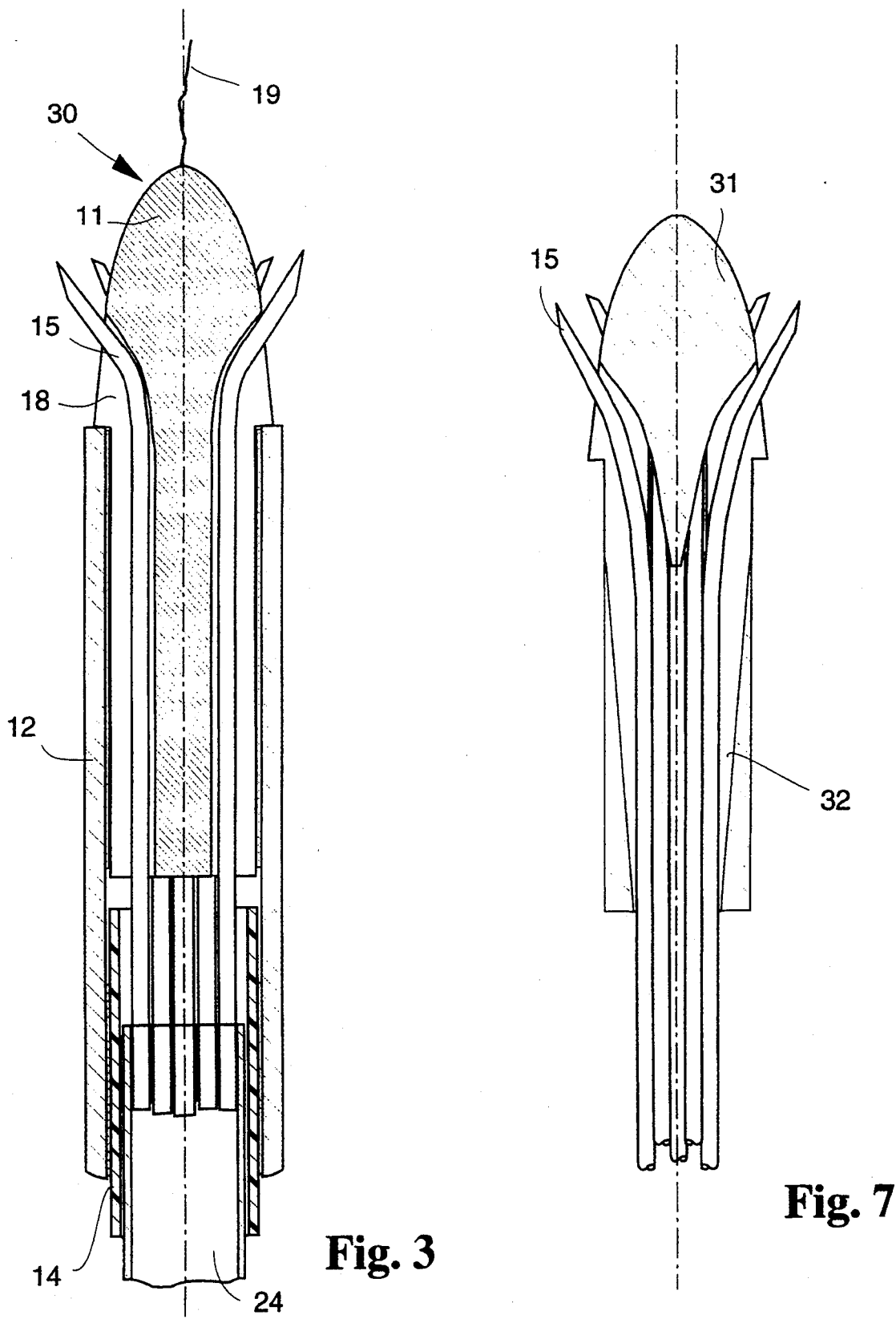
FIG. 3 shows a catheter tip fixedly connected to a single lumen stem movably supporting therein a flexible tube which has secured thereto a bundle of injection needles movably guided in the catheter tip.

FIG. 3 illustrates still a further embodiment of the invention wherein the bundle of injection needles 15 is axially movable inside the single-lumen stem 14, and the catheter tip 11 is fixedly connected to the single-lumen stem 14 through the retainer sleeve 12. Disposed within the single-lumen stem 14 is a flexible tube 24 which has rear portions of the injection needles 15 inserted into and secured, i.e. cemented or soldered, to a front portion of the tube so that axial movement of the flexible tube 24 within the single-lumen stem 14 in opposite directions will cause the injection needles to be retracted into or extended from, respectively, the catheter tip 11. In order to give the distal end structure a high degree of flexibility, the distance between the catheter tip 11 and the flexible tube 24 can be substantially greater than depicted in FIG. 3; which means that, in deviation from what is shown, the retainer sleeve 12 does not extend to the region in which the flexible tube 24 is movable. In order to improve sliding ability, the flexible tube 24 preferably is coated with an antifriction material, such as PTFE, for example. The same applies with respect to the injection needles movable in the multi-lumen stem shown in FIG. 1 and in the single-lumen stem shown in FIG. 2.

Figure 4:
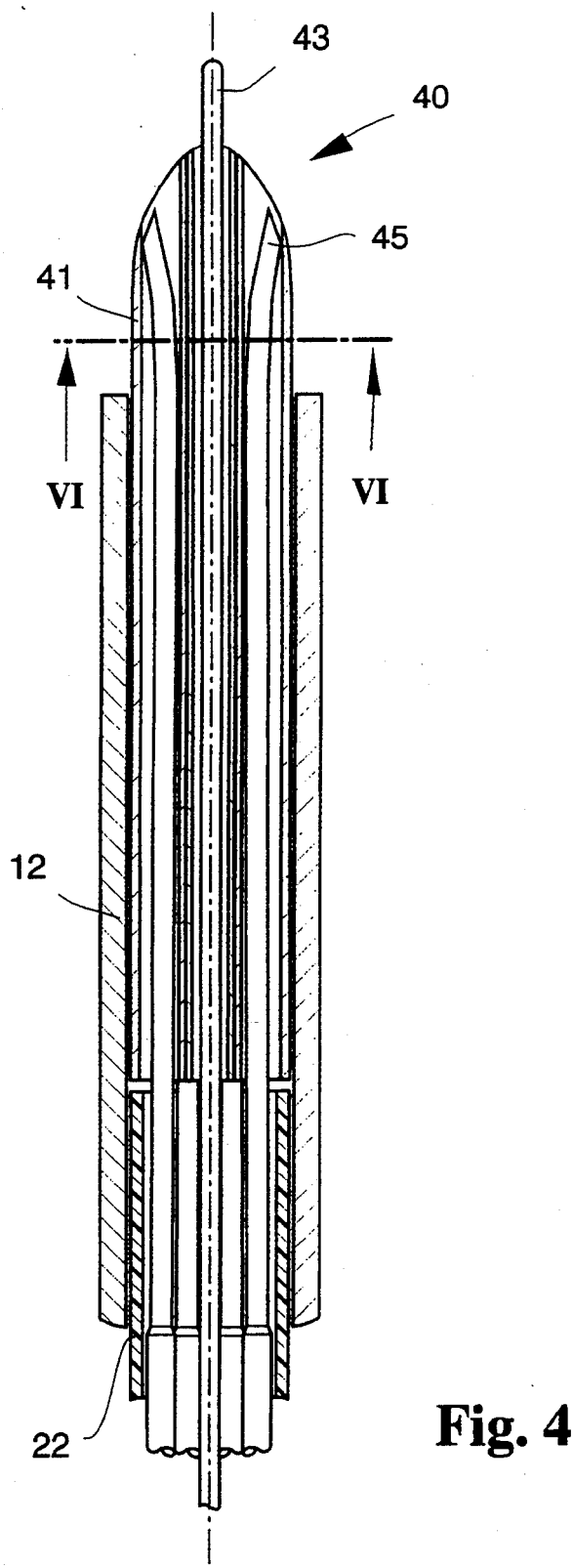
Figure 6:
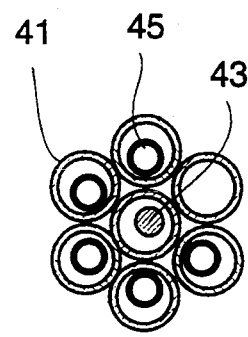
FIG. 6 is a cross-sectional view, taken along line VI—VI in FIG. 4, of the catheter tip composed of a bundle of tubes.

FIG. 4 shows still another embodiment of the invention wherein the distal end structure 40 of the catheter includes a catheter tip consisting of a bundle of tubes 41 (see also FIG. 6) which extend to a single-lumen tube 22 fixedly connected to the catheter tip through the retainer sleeve 12. The pre-bent injection needles 45 extend through, and are axially movably in the single-lumen tube 22 and the individual tubes 41. The injection needles have a smaller diameter in the regions of the catheter tip and single-lumen stem 22 than throughout the remaining part of the catheter, which makes the front ends of the injection needles highly flexible whilst at the same time assuring optimal stiffness and flexibility in the region of the catheter stem. The injection needles which are slidably supported in the single-lumen stem 22 preferably are coated with a suitable antifriction material. A center lumen within the bundle of injection needles 45 is preferably left free to accommodate a guide wire 43 which extends further into a corresponding tube within the tube bundle 41 and can protrude therefrom at the front end of the catheter. In order to reduce internal friction and to allow medication to be injected at a lower pressure, the portions of the injection needles 45 having the larger outer diameter may also have an inside diameter which is larger than that of the needle points. Although FIG. 4 depicts the larger-diameter sections of the injection needles likewise as spaced from the catheter tip a relatively short distance, it will be understood that these thicker sections of the needles should preferably be spaced from the support sleeve 12 a greater distance in the interest of increased flexibility at the catheter tip.

Figure 5:
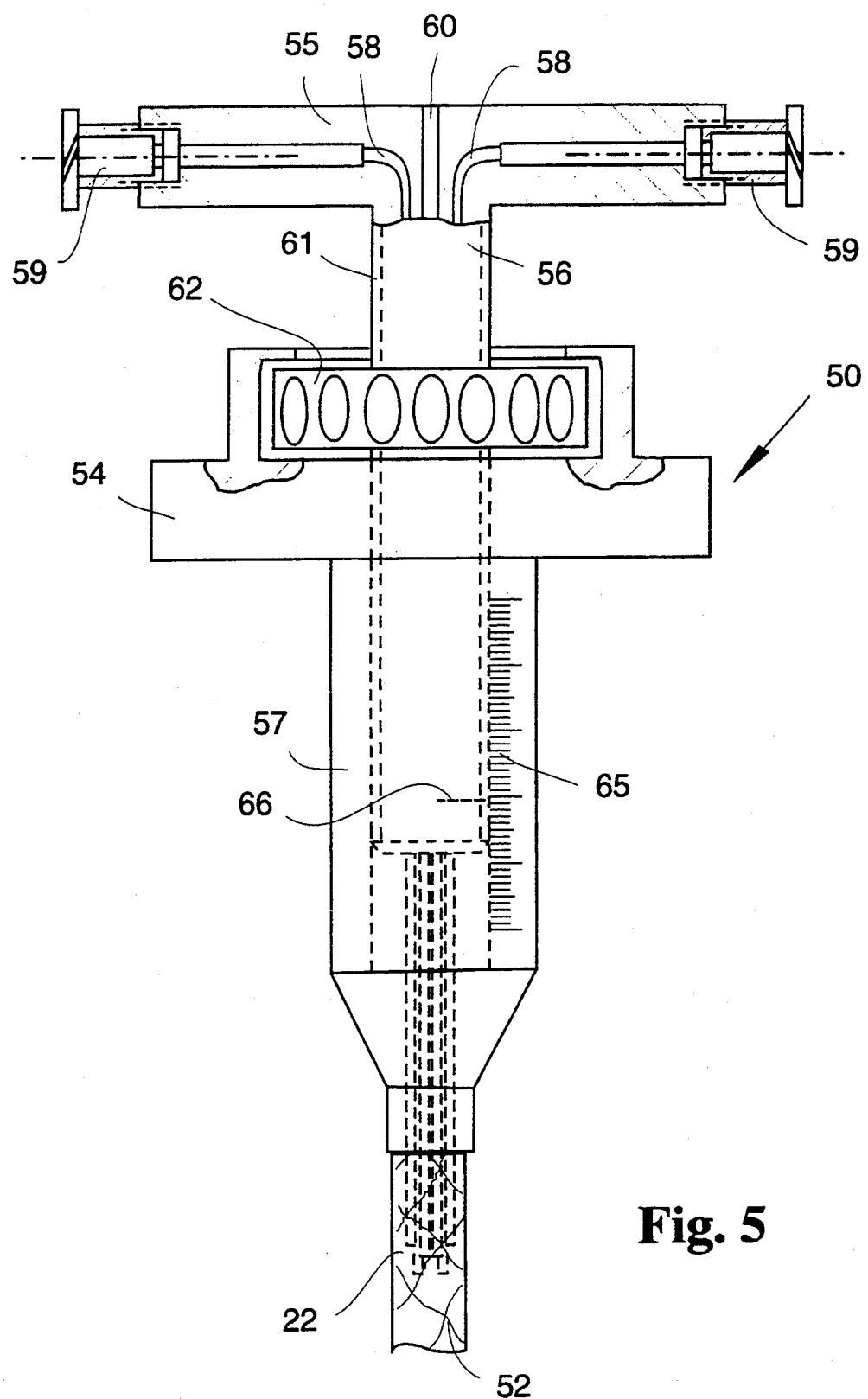
FIG. 5 shows an operating device for displacing a bundle of injection needles within a single-lumen stem.

Referring now to FIG. 5 of the drawings, there is shown therein an operating device for effecting extension of the injection needles. This operating device, generally designated with numeral 50, comprises essentially two parts 54 and 55 referred to herein as the stationary part 54 and as the movable part 55, respectively. The movable part 55 includes a thrust plunger 56 which is slidable in a cylinder 57 of the stationary part 54 and has connected thereto the extracorporal ends of the injection needles, the movable part 55 includes medication inlets 59 and bores 58 providing fluid flow communication between the medication inlets 59 and the corresponding injection needles. The movable part 55 further includes a bore 60 which extends into the guide volume within the catheter stem. The thrust plunger 56 has a thread threadedly engaged with a knurled nut 62 which is captively supported on the stationary part 54 and rotatable to displace the thrust plunger 56 inwardly of the cylinder 57 and thereby effect a corresponding movement of the injection needles connected thereto. The cylinder 57 may be provided with a scale 65 and the thrust plunger 56 with an indicating line 66 for indicating the extent of plunger displacement and thereby allowing it to be accurately controlled. The cylinder 57 has connected thereto the catheter stem 22 which may have a stainless-steel wire mesh 52 incorporated therein in order to stabilize it against undesirable longitudinal elongation and compression while the injection needles are being displaced. It should be noted that the operating device as illustrated in the drawing is specially adapted for use with a catheter employing a distal end structure such as hereinbefore described with reference to FIG. 4.

If to be used together with a catheter employing a distal end structure such as shown in FIG. 3, the operating device 50 will have the flexible tube 24 instead of the bundle of injection needles connected to its thrust plunger 56, and there will be provided only one medication inlet 59 which will be in fluid flow communication with the space within the flexible tube 24.

A catheter utilizing a distal end structure such as shown in FIG. 1 or 2 will have the extracorporal ends of the injection needles connected to the stationary part 54 of the operating device 50 which, for this purpose, will have corresponding medication inlets formed therein. The movable part 55 of the operating device will, in this case, act upon the operating wire 17 to effect longitudinal movement of the catheter tip 11 of the distal end structure.

Although not shown in the drawings, the guide lumen for the guide wire may have its outlet located, not at the operating device, but ahead of it in the extracorporal region of the catheter stem, for which purpose the guide lumen is arranged eccentrically between the bundle of injection needles and the outer stem.

Figure 8:
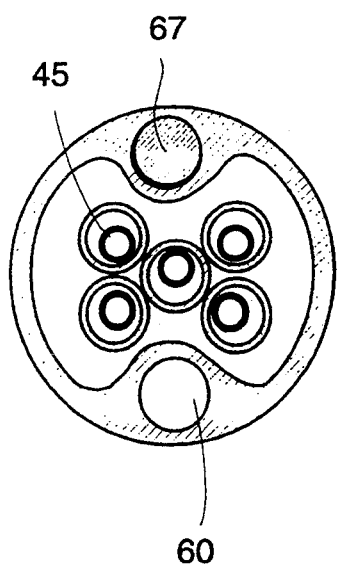
FIG. 8 is a cross-sectional view of a catheter stem containing needle and guide lumina

Furthermore, the stem of the catheter may have connected thereto a stabilizing wire which may be either molded into the outer jacket of the stem or, if the stem is a multi-lumen stem, may be mounted, preferably glued, in place within a lumen. In FIG. 8 which is a cross-sectional view of a catheter having a single-lumen stem, the two lumina for the guide wire and the stabilizing wire are shown, by way of example, as molded into peripheral wall portions of the stem, whereas the bundle of injection needles is arranged to be freely movable within the stem.

The catheter tip can be made from various materials, plastics as well as metal, ceramics or glass, and desirable maybe of a radio-opaque design.

Furthermore, the lumina which are movable within the catheter preferably are sealed within the catheter against liquid reverse flow, for example by means of suitable lubricants.

In order to stabilize the catheter stem, the latter may be torsioned; and in order to ensure that the injection needles will emerge from the catheter tip smoothly, the bundle of injection needles may be arranged within the catheter stem along an elongated helix. This will result in improved movability, especially if employed in combination with friction-reducing lubricants.

The functional operation of the injection catheter can be optimized by attaching to the catheter, in a previously proposed manner, balloons adapted to fix the catheter in position during an injection. Angioplastic balloons arranged distally as well as proximally with respect to the catheter tip will also improve the applicability of the catheter and, in particular, may help to enable a balloon dilatation to be performed simultaneously with an injection of medication into the affected tissue.

What is claimed is:

1. A catheter for injecting a fluid or medication into hollow organs and body cavities, particularly into coronary vessels and arteries, comprising: a front end with a catheter tip adapted to be inserted into arteries and an extracorporal end opposite said catheter tip; a catheter stem extending between said catheter tip and said extracorporal end; a plurality of injection needles arranged in a bundle and firmly mounted in said catheter stem and having needle points arranged in the catheter tip for relative movement of said tip with respect to said injection needles, said injection needle points, in a retracted position, lying inside the catheter tip and, in an extended position, lying exposed in readiness for applying said fluid or medicine; an operating device connected to the extracorporal end of the catheter and an operating wire extending through said bundle and being connected to said catheter tip and being operable to effect movement of said catheter tip; and openings formed in the catheter tip allowing the needle points to protrude therefrom laterally as well as forwardly when said catheter tip is retracted; said catheter stem including said lumen and said needles being connected to one part of the operating device and the operating wire being connected to the other part thereof, the arrangement being such that movement of one of said two parts in a predetermined direction relative to the other effects a corresponding relative movement between the catheter tip and the injection needles.

2. A catheter according to claim 1, wherein the injection needles joined together as a bundle are inserted, behind the distal region of the catheter, into and connected to a flexible tube of larger inside diameter, and that, together with said tube, they are axially movable within the catheter stem.

3. A catheter according to claim 1, wherein the injection needles have a reduced wall thickness, but the same flow cross-section, in the distal region thereof.

4. A catheter according to claim 1, including a guide wire which is guided in a guide lumen defined within said bundle of injection needles.

5. A catheter according to claim 4, wherein said guide lumen extends eccentrically between said bundle of needles and the catheter stem, said guide lumen opening outwardly at an extracorporal location before the operating device.

6. A catheter according to claim 1, wherein the catheter tip has a guide wire connected thereto at the distal end thereof.

7. A catheter according to claim 1, wherein the bundle of injection needles is disposed in a lumen fixed in position within the catheter stem, said operating wire extending through said lumen for retracting and extending the catheter tip respectively into and from the catheter stem.

8. A catheter according to claim 1, wherein the catheter tip consists of a bundle of stainless-steel tubes defining lumina which having the injection needles and, a guide wire extending therethrough.

9. A catheter according to claim 1, wherein the catheter tip has formed therein a central bore and guide grooves communicating therewith, said bundle of injection needles extending through said central bore and being laterally extendible through said guide grooves.

10. A catheter according to claim 1, wherein the catheter stem has a stainless-steel wire mesh molded therein.

11. A catheter according to claim 1, wherein one of said catheter stem and said multi-lumen bundle has a stabilizing wire incorporated therein.

12. A catheter according to claim 1, wherein said operating device includes a thrust plunger for effecting displacement of the injection needles or said operating wire, said thrust plunger having a threaded portion which is threadedly engaged with a knurled nut operable to effect axial displacement of the thrust plunger, and said operating device including medication inlets which communicate with the individual injection needles.

* * * * *